United States Patent [19]

Schreiber

[11] Patent Number: 4,908,358
[45] Date of Patent: Mar. 13, 1990

[54] INHIBITION OF IMMUNE CLEARANCE USING PROGESTERONE ANALOGUES

[75] Inventor: Alan D. Schreiber, Philadelphia, Pa.

[73] Assignee: Trustees of The University of Pennsylvania, Philadelphia, Pa.

[21] Appl. No.: 159,706

[22] Filed: Feb. 24, 1988

Related U.S. Application Data

[63] Continuation-in-part of Ser. No. 89,790, Aug. 27, 1987.

[51] Int. Cl.⁴ ............................................. A61K 31/56
[52] U.S. Cl. .................... 514/177; 514/178; 514/885
[58] Field of Search .................. 514/177, 178, 181; 435/13; 260/397.3

[56] References Cited

U.S. PATENT DOCUMENTS 2,648,662  8/1949  Julian et al.
3,463,852  8/1969  Reiman et al. .................. 514/178
4,701,450 10/1987  Kelder et al. .................. 514/177

FOREIGN PATENT DOCUMENTS 1124906 11/1984. European Pat. Off. ............ 514/177

OTHER PUBLICATIONS

Jungers et al., Hormonal Modulation in Systemic Lupus Erythematosus; Arthritis and Rheumatism 28: 1243–1249 (1985).
Friedman et al., Effect of Estradiol and Steroids on the Clearance of Immunoglobulin G–Coated Erythrocytes; J. Clin. Invest. 75: 162–167 (1985).
Nettl et al., The Effect of Endogenous and Synthetic Steroids on the Clearance of IgG and/or C3 Coated Cells; Blood Abs #264 (1984 suppl).
Shear et al., Clearance of Sensitized Erthrocytes in NZB/NZW Mice Effects of Castration and Sex Hormone Treatment; Eur. J. Immunol. 11:776 (1981).
Bach, J. F.; John Wiley & Sons (NY); "Immunology", p. 812 (1982), AHN et al; Danzol for the Treatment of Idiopathic Thrombocytopenic Purpura, N. Eng. J. Med., p. 1396 (1983).
Roubinian et al.; Androgenic Hormones Modulate Antibody Responses and Improve Survival in Murine Lupus; J. Clin. Inquist. 59:1066 (1977).
Siitri et al.; Sex Steroids and the Immune System, J. Steroid Biochem. 12:425–432 (1980).
Duncan et al.; An In Vivo Study of the Action of Antiglucocorticoids on Thymus Weight Ratio . . . J. Steroid Biochemistry 10:245–259 (1979).
Schreiber et al., "Effect of Danazol in Immune Thrombocytopenic Purpura", N. Engl. J. Med. 316: 503–508 (02/26/87).

(List continued on next page.)

Primary Examiner—H. M. S. Sneed
Assistant Examiner—J. Saba
Attorney, Agent, or Firm—Woodcock Washburn Kurtz Mackiewicz & Norris

[57] ABSTRACT

Methods of modulating the clearance of antibody-coated cells from the circulation of mammals are disclosed. A compound having the formula

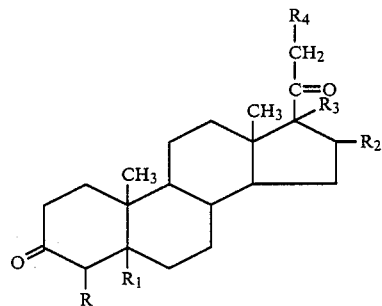

wherein R and $R_1$ individually are hydrogen or taken together form a double bond;
$R_2$ is hydrogen or methyl; $R_3$ is hydrogen or hydroxyl; and $R_4$ is hydrogen or hydroxyl is administered in an amount effective to modulate the clearance of antibody-coated cells from the bloodstream of the mammals.

4 Claims, 2 Drawing Sheets

OTHER PUBLICATIONS

Dougados et al., *Arthritis Rheum.* (Suppl) 28: 246 (1985).

Fretwell et al., *J. Allergy Clin. Immunol* 69: 306–310 (1982).

Terenius, "Affinities of Progestogen and Estrogen Receptors in Rabbit Uterus for Synthetic Progestogens", *Steroids* 23(6): 909–919 (1974).

DiSorbo et al., "Glucocorticoid Activity of Various Progesterone Analogs: Correlation Between Specific Binding Thymus and Liver and Biologic Activity", *Ann N.Y. Acad. of Sci.* 206: 355–368 (1977).

Schreiber et al., *J. Clin Invest.* 51: 575 (1972).

Atkinson et al., "Effects of Corticosteroids and Splenectomy on the Immune Clearance and Destruction of Erythrocytes", *J. Clin. Invest.* 52(6): 1509–1517 (1973).

Schreiber et al., "Role of Antibody and Complement in the Immune Clearance and Destruction of Erythrocytes", *J. Clin. Invest.* 51: 583–589 (1972).

Sanders et al., "Hormonal Modulation of Modulation Clearance of IgG Sensitized Cells", Association of American Physicians (Abstract).

INHIBITION OF IMMUNE CLEARANCE USING PROGESTERONE ANALOGUES

REFERENCE TO GOVERNMENT GRANTS

The invention described herein was supported in part by National Institutes of Health grants AI-22193 and HL-28207. The United States Government has certain rights in the invention.

CROSS-REFERENCE TO RELATED APPLICATIONS

This application is a continuation-in-part of application Ser. No. 089,790, filing date 8/27/87. This application is also related to pending application Ser. No. 030,028 filed Mar. 24, 1987. It is related to an application entitled "Methods of Treating diseases Characterized By Interactions Of IgG-Containing Immune Complexes With Macrophage Fc Receptors Using Antiestrogenic Benzothiophenes" (attoreny docket number UPN-83) which is being filed concurrently herewith.

FIELD OF THE INVENTION

The invention relates to the treatment of mammalian disease characterized by interactions of IgG-containing immune complexes and macrophage Fc receptors, and in particular to the modulation of the clearance of antibody-coated cells from the circulation of mammals.

BACKGROUND OF THE INVENTION

Glucocorticoids have been widely employed in the treatment of immunologic disorders. Other steroid hormones, such as sex steroids, may also influence the clinical expression of immunologic disease. For, example, estrogens and their analogues have several known effects on the immune system. This group of sex hormones appears to increase the production of serum globulins, increase the phagocytic nature of mononuclear cells, increase the clearance of IgG-coated cells by splenic macrophages, and bind to and alter the functions of suppressor T-cells.

In autoimmune diseases such as thrombocytopenic purpurea (ITP) there is an increased clearance of platelets by macrophages in the spleen. ITP is believed to be caused by antiplatelet antibodies, which are freqently of the IgG class. These antibodies bind to the platelets forming IgG containing immune complexes. Levels of IgG on the platelet surface are generally elevated in patients with ITP; a change in the level of platelet-bound IgG in a given patient is often associated with a change in the platelet count with increases in bound IgG generally correlating with decreased platelet levels. The level of platelet-associated IgG, however, does not correlate uniformly with the platelet count in ITP. One explanation for this discrepancy may be differences in the rate or extent of clearance of platelets that is initiated by the adherence of IgG-coated platelets to surface Fc (IgG) receptors on tissue macrophages. For example, the rate of platelet clearance may be affected by processes that alter the capacity of macrophage Fc (IgG) receptors to recognize the IgG ligand.

In the spleen, IgG-containing immune complexes bind by the Fc region of IgG to macrophages at Fc receptor sites on the macrophage surface. The Fc portion of the immunoglobulin molecule (identified by papain cleavage) is believed to be responsible for biological activity other than antigen binding. The Fc portion is apparently responsible for complement fixation, transplacental transfer, binding to cells such as macrophages and granulocytes and the rate of synthesis and catabolism of the immunoglobulin molecule.

Expression of monocyte receptors for monomeric IgG varies widely among patients with ITP as compared with healthy donors. This variation in receptor expression may result from acquired changes in macrophage function or may reflect a more basic genetic disturbance. There is some evidence that the prevalence of ITP may be increased in several genetic subgroups. Abnormalities in the expression of function of Fc(IgG) receptors have been observed in association with certain HLA haplotypes. Moreover, both decreased numbers of C3b receptors (CR1) and uncommon CR1 allotypes have been noted in patients with systemic lupus erythematosus and members of their families. An increase in the number of Fc (IgG) receptors for monomeric IgG has been noted on the monocytes of patients with immune hemolytic anemia. These observations suggest that there may be a fundamental disturbance in the expression of monocyte or macrophage Fc (IgG) receptors in certain patients with ITP or other immunologic disorders.

An increase in the number of density of monocyte or macrophage Fc (IgG) receptors may result from the elaboration of such mediators as gamma interferon during an immune response or infection or the release of bacterial products. Alternatively, a decrease in the number of Fc (IgG) receptors available to bind IgG may result from their occupancy by circulating immune complexes that may be present in patients with ITP.

Autoimmune diseases are those diseases in which the body's mechanisms for distinguishing itself from foreign invaders has malfunctioned in some way. Typically, the body begins to make antibodies to certain parts of itself; these antibodies trigger the immune system which then destroys the tissue identified by the abnormal antibodies. Autoimmune diseases have varied focal points of attack. The autoimmune hemolytic anemias represent a group of disorders in which individuals produce antibodies to one or more of their own erythrocyte membrane antigens. Coating of erythrocytes by the abnormal antibodies is followed by their clearance from the circulation by splenic macrophages and subsequent destruction in the spleen. Representative diseases in this class are immune hemolytic anemia, immune thrombocytopenic purpura and autoimmune neutropenia. Another type of autoimmune disease is the type represented by systemic lupus erythematosus and rheumatoid arthritis. In these diseases, chronic inflammation is present in the joints, tendons, kidneys, lung, heart and other organs. In rheumatoid arthritis, for example, breakdown of joint cartilage into the synovial fluid of the joint is present in later stages of the diesase. In systemic lupus erythematosus, however, cartilage or bone degradation is not usually found. Systemic lupus erythematosus and rheumatoid arthritis are often present in conjunction with other types of autoimmune disease. In systemic lupus erythematosus and rheumatoid arthritis, tissue destruction is associated with the presence of IgG-containing complexes in the circulation. It is believed that recognition of these complexes in tissues by cells having Fc receptors initiates or increases tissue destruction by macrophages and possibly other cells such as polymorphonuclear leukocytes in these tissues.

Diseases characterized by interactions of IgG containing immune complexes with macrophage Fc receptors are often chronic and cause much suffering to victims. Treatments currently available have serious side effects.

Corticosteroids inhibit clearance of IgG-coated erythrocytes by modulating splenic macrophage $F_c(IgG)$ receptor activity. They have been used in treating autoimmune disorders such as immune thrombocytopenic purpura and systemic lupus erythematosus. However, corticosteroids have undesirable side effects such as exacerbation of diabetes, hypertension, electrolyte imbalance, increased appetite and weight gain, moonlike faces, osteoporosis, myopathy and increased susceptibility to infection. The severity of these side-effects is related to both the duration and dosage of therapy.

Progesterone has been observed to inhibit splenic macrophage clearance of IgG-coated erythrocytes by fifty percent. Nettl et al, *Blood* 64: Suppl 1:8 A (Abstract) (1984). However, progesterone is a progestational agent, and exerts substantial sex-organ hormonal effects, making its use in treatment less than optimal.

The autoimmune disease chronic immune thrombocytopenic purpura has been treated with danazol, an antigonadotropic drug. Ahn et al, *N. Engl. J. Med.* 308: 1396–1399 (1983); Schreiber et al, *N. Engl. J. Med.* 316: 503–508 (Feb. 26, 1987). Danazol is a synthetic analogue of androgenic steroids and progesterone. As an androgen, danazol can cause masculinization. Moreover, use of this drug in treating systemic lupus erythematosus has been associated with a high incidence of side-effects such as a rise in hepatic enzymes, skin rash, weight gain, acne and myalgia. Dougados et al, *Arthritis Rheum.* (Suppl.) 28: 246 (1985); Jungers et al, *Arthritis Rheum.* 28: 1234–1250 (1985).

The synthetic hydroxyprogesterone derivative, cyproterone acetate has been used in treating female patients having moderately active systemic lupus erythematosus. Jungers et al, supra. Cyproterone acetate is an antigonadotropic agent possessing peripheral antiandrogenic effects. As an antigonadotropic agent, it affords contraception in females. Despite achieving some success in treating systemic lupus erythematosus, it is likely that cyproterone acetate has progestational activity, making it undesirable in treatment. Moreover, it has been reported that antigonadotropic drugs such a cyproterone acetate and danazol should not be used in male systemic lupus erythematosus patients. Jungers et al, supra. In males, the antigonadotropic effect of cyproterone acetate induces a marked decrease in plasma testosterone concentration. In addition, cyproterone acetate acts as an antiandrogen in displacing 5-dihydrotestosterone from a specific receptor in the prostate. According to Jungers et al, supra, administration of cyproterone acetate in male systemic lupus erythematosus patients should induce a marked fall in plasma testosterone level which could potentially provoke an exacerbation of clinically ative systemic lupus. Danazol was reported to unmask latent systemic lupus erythematosus in a male patient treated for angioneurotic edema. Fretwell et al, *J. Allergy Clin. Immunol* 69: 306–310 (1982).

The use of progesterone in inhibiting immune clearance of antibodycoated cells from the circulation, and therefore its potential use in treating disorders such as systemic lupus erythematosus, immune hemolytic anemia and immune thrombocytopenic purpura, is unattractive because of progesterone's sex-organ hormonal effects. There is a need, therefore, for treatments for diseases characterized by interactions of IgG-containing immune complexes with macrophage Fc receptors which have the immune clearance modulating activity of progesterone without the progestational sex-organ hormonal effects of progesterone and the side-effects of other treatments. Accordingly, it is an object of the invention to provide methods of treating these diseases without the undesired effects discusses above.

SUMMARY OF THE INVENTION

Methods of modulating the clearance of antibody-coated cells from the bloodstream of mammals are provided. A compound having the formula I

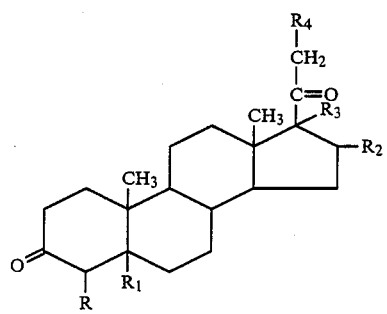

wherein R and $R_1$ individually are hydrogen or taken together form a double bond;

$R_2$ is hydrogen or methyl; $R_3$ is hydrogen or hydroxyl; and $R_4$ is hydrogen or hydroxyl is administered to the mammal in an amount effective to modulate clearance of antibody coated cells from the circulation of the mammal. In preferred embodiments of the invention, modulation of the clearance of antibody-coated cells from the circulation of the mammal is accomplished by inhibition of clearance. Preferred compounds for use in the invention are 17-α-hydroxyprogesterone (or 4-pregnen-17-α-ol-3,20-dione), in accordance with formula II;

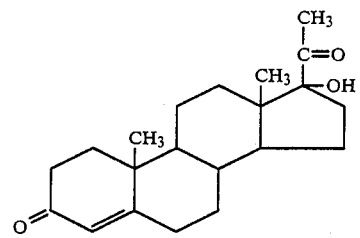

16-α-methylprogesterone (or 4-pregnen-16-α-methyl-3,20-dione), in accordance with formula III;

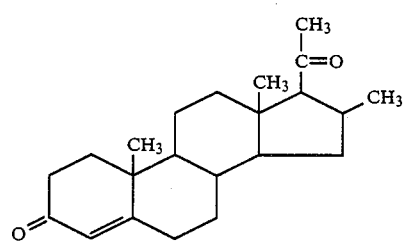

cortexolone (or 17,21-dihydroxypregn-4-ene-3,20-dione), accordance with formula IV;

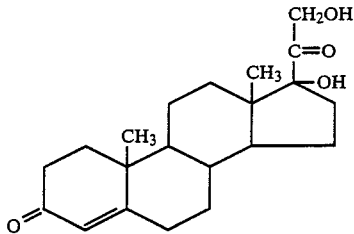

and; 5-α-pregnan-3,20-dione, in accordance with formula V;

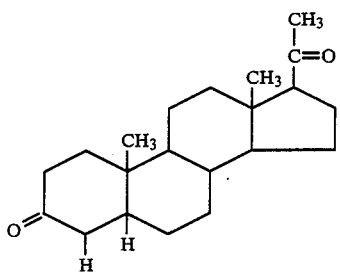

The invention also provides methods for treatment of mammalian diseases characterized by interactions of IgG-containing immune complexes with macrophage Fc receptors. A compound in accordance with formula I

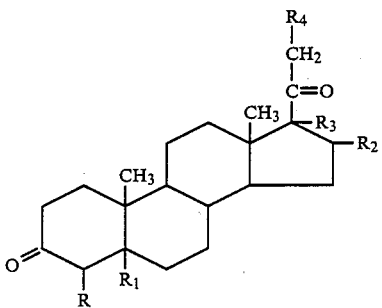

wherein R and $R_1$ individually are hydrogen or taken together form a double bond;

$R_2$ is hydrogen or methyl; $R_3$ is hydrogen or hydroxyl; and $R_4$ is hydrogen or hydroxyl is administered to the mammal in an amount effective to modulate the clearance of antibody-coated cells from the bloodstream of the mammal. In preferred embodiments of the invention, modulation of the clearance of antibody-coated cells from the circulation of the mammal is accomplished by inhibition of clearance. Preferred compounds for use in the invention are those having formulas II through V.

In diseases characterized by interactions of IgG-containing immune complexes with macrophage receptors, clearance of antibody-coated erythrocytes may be elevated above normal levels. The compounds useful in the invention, which are listed above, modulate the excessive clearance of antibody-coated cells from the bloodstream of the mammal. It is believed that these compounds modulate the clearance of antibodycoated cells by inhibiting the clearance of IgG-containing immune complexes from the bloodstream which is initiated by interactions of these complexes with macrophage Fc receptors in the spleen of the mammal. It is believed that the compounds useful in the invention modulate the effects of estrogen and estrogen derivatives upon the macrophage Fc receptors. It is also believed that the receptors themselves may be altered or in some way malfunctioning in these diseases which are characterized by interactions of IgG-containing immune complexes with macrophage Fc receptors.

DETAILED DESCRIPTION OF THE INVENTION

Figure 1:
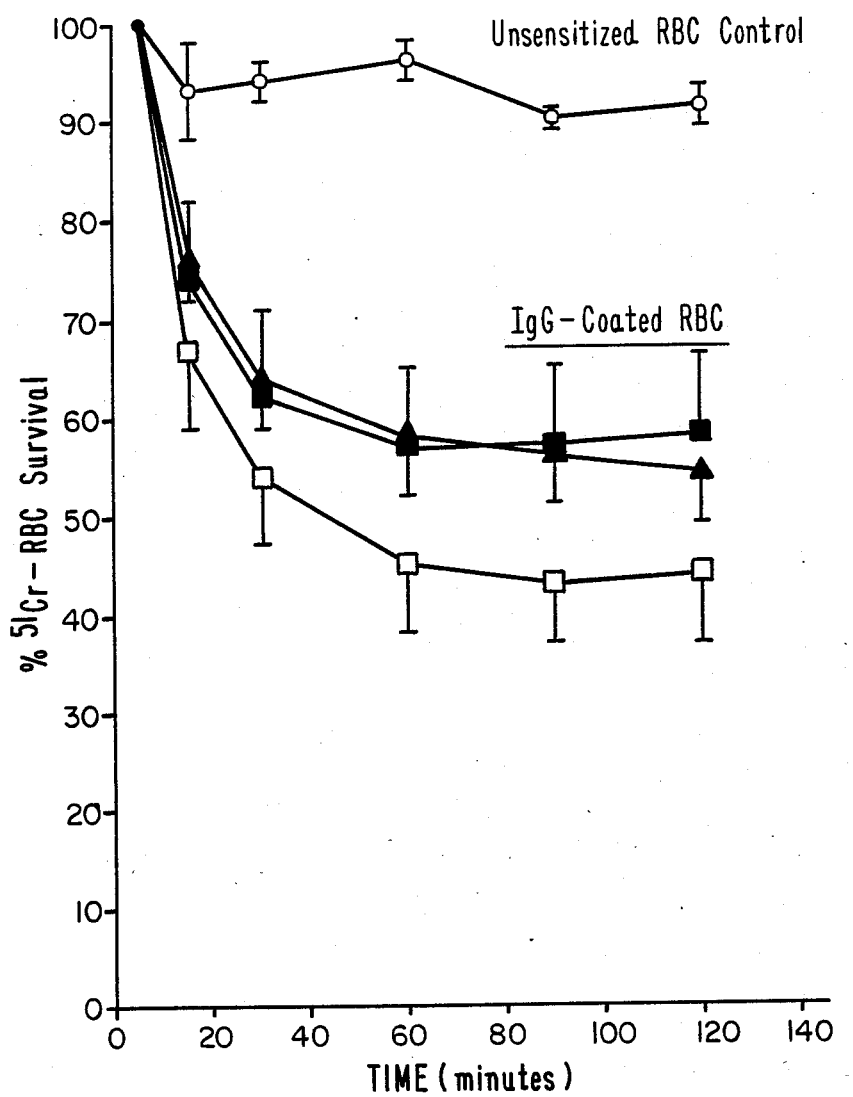
FIG. 1 is a plot of the clearance of the following $^{51}Cr$-radiolabeled cells from the circulation of guinea pigs as a function of time:
  uncoated guinea pig erythrocytes from untreated animals (open circle data points);
  IgG-coated guinea pig erythrocytes from untreated animals (open square data points);
  IgG-coated guinea pig erythrocytes from 17-α-hydroxyprogesterone-treated animals, 90 mg/kg/day (solid square data points) and 10 mg/kg/day (solid triangle data points).

Progesterone derivatives which have little or no sex-organ effects and which modulate the clearance of antibody-coated cells from the circulation of mammals are useful in the practice of the invention. Compounds which are preferred for use in the invention are described below. As used herein, the terms erythrocytes, red blood cells and RBC are equivalent terms for erythrocytes.

17-α-hydroxyprogesterone is a naturally-occurring progesterone analogue. It may be prepared, for example, according to U.S. Pat. No. 2,648,662. 16-α-methylprogesterone (Steraloids, Inc.) is a synthetic progesterone analog. Cortexolone (Steraloids, Inc.)is structurally identical to cortisol but for the absence of an hydroxyl at C-11. 5-α-pregnan-3,20-dione (Steraloids, Inc.) is structurally identical to progesterone but for the $C_4$–$C_5$ double bond and has minimal progestogen effect. Terenius et al, Steroids 23(6): 909–919 (1974), reported that 17-α-hydroxyprogesterone has lower progesterone receptor affinity than progesterone as well as lower progestational activity in in vitro experiments using rabbit uteri. This compound, while substantially lacking the sex-organ hormonal effects of progesterone, has now been discovered to have immune clearance inhibiting activity.

The glucocorticoid effects of cortexolone, 17-α-hydroxyprogesterone and 16-α-methylprogesterone have been studied by DiSorbo et al., Ann N. Y. Acad of Sci 206: 355–368,(1977). Cortexolone was found to have antiglucocorticoid activity in vitro but no glucocorticoid activity in vivo. 16-α-methylprogesterone and 17-α-hydroxyprogesterone showed antiglucocorticoid activity in vitro but failed to elicit either glucocorticoid or antiglucocorticoid activity in vivo in rats.

The compounds useful in the practice of this invention may be administered in dosages sufficient to achieve the desired modulation of clearance. In general, doses of from about 1.0 mg/kg/day to about 90 mg/kg/day have been found to be preferred. Immune clearance of antibodycoated cells may be achieved by administering the subject compounds by any convenient route. While parenteral administration is preferred, the compounds may be formulated for oral administration in the form of capsules, tablets, or the like or other forms of administration.

The autoimmune hemolytic anemias represent a group of disorders in which individuals produce antibodies directed to one or more of their own erythrocyte membrane antigens. Coating of erythrocytes by antibodies is followed by their clearance from the circulation by splenic macrophages, and subsequent destruction in the spleen. As with human erythrocytes, guinea pig erythrocytes sensitized with IgG antibodies are cleared by macrophages in the spleen. Because of such similarities to man, the guinea pig is an accepted animal model for experimental study of autoimmune diseases, in particular autoimmune hemolytic anemia.

It is believed that 17-α-hydroxyprogesterone, 16-α-methylprogesterone, 5-α-pregnan-3,20-dione and cortexolone are useful in treating diseases characterized by interactions of IgG containing immune complexes with macrophage Fc receptors. These include autoimmune disorders such as immune hemolytic anemia, immune thrombocytopenic purpura, and perhaps autoimmune neutropenia. They may also prove to be useful in treating other autoimmune disorders such as systemic lupus erythematosus and rheumatoid arthritis.

The dosage and dosage regimen is selected to result in clinical response. For example, in the case of autoimmune hemolytic anemia or immune thrombocytopenic purpura, clinical response is evidenced by a rise in blood count. Once a clinical response is achieved and the patient stabilizes, tapering of treatment should begin. This may take several months. Alternate day (every other day) therapy may be effective in some patients after the clinical course of the disease stabilizes.

EXAMPLE 1

The immune clearance inhibiting activity of 17-α-hydroxyprogesterone and 16-α-methylprogesterone, and thus their utility in treating diseases characterized by interactions of IgG containing immune complexes with macrophage Fc receptors, is demonstrated by an animal model of immune hemolytic anemia established by Schreiber, et al, *J. Clin. Invest* 51: 575 (1972).

Progesterone, 17-α-hydroxyprogesterone and 16-α-methylprogesterone were each reconstituted in a steroid suspending vehicle consisting of 0.5% carboxylmethylcellulose, 0.4% Tween 80 (surfactant), and 1.5% ethanol in isotonic saline as described by Friedman et al, *J. Clin. Invest.* 75: 162–167 (1985). The two progesterone analogues were obtained from Steraloids, Inc. (Wilton, N.H.). Male and non-pregnant female Hartley guinea pigs weighing 500–600 g,(Dutchland Farms, Denver, Pa.) received injections of equal volumes of one of the steroid preparations or 1 ml of a sham preparation consisting of the steroid suspending vehicle without steroid. All animals were injected subcutaneously in the dorsal neck fat pad.

The clearance of IgG-coated erythrocytes was determined in all animals using erythrocytes sensitized with rabbit anti-guinea pig erythrocyte antibody. Rabbit IgG and IgM anti-guinea pig erythrocyte antibody was prepared in rabbits according to standard procedures. The IgG fraction was isolated by Sephadex G200 chromatography. Friedman et al, *J. Clin. Invest.* 75: 162–167 (1985). Guinea pig erythrocytes were obtained by cardiac puncture, washed, and radiolabeled with $^{51}$Cr-sodium chromate (New England Nuclear, Boston, MA). An aliquot of the radiolabeled erythrocytes was sensitized with rabbit anti-guinea pig erythrocyte IgG antibody so as to coat each cell with approximately 6,000 molecules of IgG antibody per erythrocyte.

$2.7 \times 10^8$ antibody-coated (or control) radiolabeled red blood cells were injected intravenously into steroid- or sham-treated animals. Samples of blood were obtained from the retroorbital space 5–120 minutes after injection, and the radioactivity of each sample was measured using a gamma counter (Gamma 8000, Beckman Instruments, Inc., Fullerton, CA). The percentage of inhibition of clearance of antibody-coated cells was calculated according to the formula:

$$\% \text{ Inhibition of Clearance} = 1 - \frac{cpm_c - cpm_x}{cpm_c - cpm_{ea}} \times 100$$

where $cpm_c$ is the blood radioactivity in counts per million of untreated control animals injected with unsensitized cells;

$cpm_x$ is the blood radioactivity in counts per million of steroid-treated animals injected with sensitized cells; and $cpm_{ea}$ is the blood radioactivity in counts per million of the sham-treated animals receiving sensitized cells.

The above formula compares immune clearance in treated animals and untreated animals studied on the same experimental days. The data is expressed as a percent alteration of clearance, where 100% inhibition of clearance by a steroid corresponds to the situation in which the clearance of antibody-sensitized erythrocyte ($cpm_x$) is identical to that of unsensitized erythrocytes ($cpm_c$). It is readily understood that if the effect of a steroid treatment is identical to the sham treatment, the mathematical expression equals zero.

Separate groups of animals were treated for seven days with (i) 10 mg/kg/day progesterone, or (ii) 90 mg/kg/day progesterone, or (iii) 10 mg/kg/day 17-α-hydroxyprogesterone, or (iv) 90 mg/kg/day 17-α-hydroxyprogesterone, or (v) steroid suspending vehicle (sham).

Guinea pigs treated with progesterone for 7 days exhibited impaired splenic clearance of IgG coated erythrocytes. Pretreatment with 90 mg/kg of progesterone inhibited the clearance of IgG coated erythrocytes in 6/6 animals (p<0.05) by 43±7% compared with simultaneous sham treated controls. At 2 hours, 50±4% of the IgG coated erythrocytes remained in the circulation in the progesterone treated animals compared with 28±4% in sham controls.

The effect of 17-α-hydroxyprogesterone on the clearance of IgG-coated erythrocytes is compared to sham-treated controls in FIG. 1. The data in the Figure is expressed as mean ±SEM (standard error the mean) Pretreatment for 5–7 days with 90 mg/kg/day of 17-α-hydroxyprogesterone impaired immune clearance in 6/7 animals (p<0.05) by 40±10% compared with simultaneously treated sham controls (Figure). Animals treated with 17-α-hydroxyprogesterone for 5–7 days at 10 mg/kg/day also demonstrated impaired clearance (5/6 guinea pigs by 41±10%; p<0.05). At 2 hours, 54±5% of the IgG coated cells from animals treated with 90 mg/kg and 58±8% of the cells from animals treated with 10 mg/kg remained in the circulation, compared to 44±7%, in sham controls (FIG. 1).

Data from experiments using 16-α-methylprogesterone indicate that this analogue also inhibits splenic clearance of IgG-coated cells. At 2 hours, 56±11% of cells in animals treated with 16-α-methylprogesterone (90 mg/kg) remained in the circulation, compared with 45±10% of the cells in the simultaneously treated sham controls. The results indicate that animals receiving the progesterone analogue 17-α-hydroxyprogesterone have impaired immune clearance compared to shamtreated controls to substantially the same extent as progesterone, notwithstanding the lack of progestational effect. Animals receiving 16-α-methylprogesterone exhibited a somewhat lesser impairment of immune clearance.

EXAMPLE 2

Figure 2:
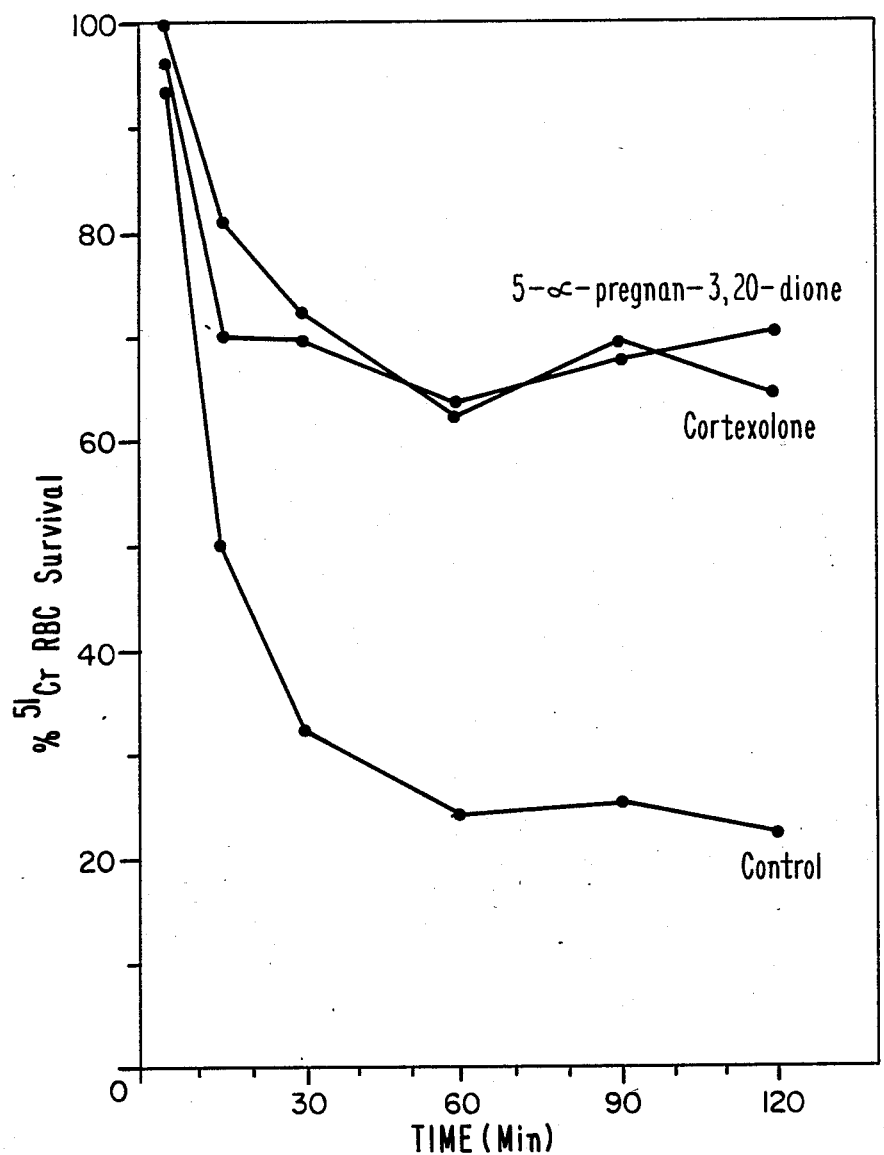
FIG. 2 is a plot of the clearance of the following $^{51}Cr$-radiolabeled cells from the circulation of guinea pigs as a function of time:
  IgG-coated guinea pig erythrocytes from untreated animals (control);
  IgG-coated guinea pig erythrocytes from cortexolone treated animals; and
  IgG-coated guinea pig erythrocytes from 5-α-pregnan-3,20-dione treated animals.

Cortexolone and 5-α-pregnan-3,20-dione were tested for modulation of the clearance of antibody-coated erythrocytes using the animal model described in example 1. Cortexolone was administered for seven days at a dosage of 50 mg/kg/day. 5-α-pregnan-3,20-dione was administered for seven days at a dosage of 50 mg/kg/day. Sham treated animals received the steroid suspending vehicle for seven days. As shown in FIG. 2, sham (control) animals cleared 75±5% of IgG-coated erythrocytes at 90 minutes and 78±5% of IgG-coated erythrocytes at 120 minutes. Animals treated with cortexolone inhibited clearance of IgG-coated erythrocytes by 36±4% at 90 minutes and 31±4% at 120 minutes. Animals treated with 5-α-pregnan-3,20-dione inhibited clearance of IgG-coated erythrocytes by 41±3% at 90 minutes and 38±3% at 120 minutes.

What is claimed is:

1. A method of inhibiting the clearance of antibody-coated red blood cells from the circulation of a mammal comprising administering to a mammal exhibiting undesired clearance of antibody-coated cells an amount of 5-alphapregnan-3,20-dione effective to inhibit clearance of antibody-coated cells.

2. The method of claim 1 wherein said amount is from about 1 mg/kg/day to about 90 mg/kg/day of mammal body weight.

3. A method of inhibiting the clearance of antibody-coated red blood cells from the circulation of a mammal comprising administering to a mammal exhibiting undesired clearance of antibody-coated cells an amount of cortexolone effective to inhibit clearance of antibody-coated cells.

4. The method of claim 3 wherein said amount is from about 1mg/kg/day to about 90 mg/kg/day of mammal body weight.

* * * * *